(12) United States Patent
Dal Farra et al.

(10) Patent No.: US 8,546,335 B2
(45) Date of Patent: *Oct. 1, 2013

(54) PEPTIDIC HYDROLYZATE PROTEASOME ACTIVATORS AND COMPOSITIONS CONTAINING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 13/265,045

(22) PCT Filed: Apr. 22, 2010

(86) PCT No.: PCT/FR2010/000324
§ 371 (c)(1),
(2), (4) Date: Oct. 18, 2011

(87) PCT Pub. No.: WO2010/122244
PCT Pub. Date: Oct. 28, 2010

(65) Prior Publication Data
US 2012/0093745 A1  Apr. 19, 2012

(30) Foreign Application Priority Data
Apr. 23, 2009  (FR) .................................... 09 01978

(51) Int. Cl.
*A61K 8/64* (2006.01)
*A61Q 19/08* (2006.01)
*A61Q 17/04* (2006.01)

(52) U.S. Cl.
USPC .......................... 514/18.8; 424/70.14; 424/59

(58) Field of Classification Search
None
See application file for complete search history.

(56) References Cited

U.S. PATENT DOCUMENTS

| | | | | |
|---|---|---|---|---|
| 5,516,507 A * | 5/1996 | N'Guyen et al. | ............... | 424/59 |
| 7,220,417 B2 | 5/2007 | Nizard et al. | | |
| 2004/0136945 A1 | 7/2004 | Nizard et al. | | |
| 2005/0282747 A1* | 12/2005 | Clark et al. | ............... | 514/12 |
| 2007/0274937 A1 | 11/2007 | Dal Farra et al. | | |
| 2008/0076718 A1 | 3/2008 | Reboud-Ravaux et al. | | |
| 2009/0041866 A1 | 2/2009 | Miyata | | |
| 2009/0196837 A1 | 8/2009 | Msika et al. | | |

FOREIGN PATENT DOCUMENTS

| | | |
|---|---|---|
| FR | 2822701 | 10/2002 |
| FR | 2898808 | 9/2007 |
| FR | 2904552 | 2/2008 |
| FR | 2915378 | 10/2008 |
| FR | 2915379 | 10/2008 |
| FR | 2915380 | 10/2008 |
| FR | 2915381 | 10/2008 |
| FR | 2915382 | 10/2008 |
| FR | 2915383 | 10/2008 |
| FR | 2915384 | 10/2008 |
| WO | 02/080876 | 10/2002 |
| WO | 2005/061530 | 7/2005 |
| WO | 2005/107697 | 11/2005 |
| WO | 2006/105811 | 10/2006 |
| WO | 2007/131774 | 11/2007 |
| WO | 2008/009709 | 1/2008 |
| WO | 2008/015343 | 2/2008 |

OTHER PUBLICATIONS

Machine translated FP 2915384 A1, enclosed, pp. 1-27.*
Merck Manual Home Edition. Effects of Aging on the Skin. Oct. 2006, p. 1.*
Chronic Effects of Sunlight, from Merck Manual, Aug. 2007, pp. 1-2.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitut~ons in Each Repeat, J. Mol. BIoL (2002) 324, 373-386.*
Machine translated WO 2008/009709 A1, enclosed, pp. 1-14.*
PCT, International Search Report, International Application No. PCT/FR2010/000324 (mailed Jul. 22, 2010; published Oct. 28, 2010).
Coux, O. et al., "Structure and Functions of the 20S and 26S Proteasomes," *Ann. Rev. Biochem.*, 65, pp. 801-847 (1996).
Glickman, M. et al., "Purification and Characterization of Proteasomes from *Saccharomyces cerevisiae*," *Current Protocols in Protein Science*, published by John Wiley & Sons, Inc., pp. 21.5 through 21.5.17 (2001).
Glickman, M.H. et al., "The Ubiquitin-Proteasome Proteolytic Pathway: Destruction for the Safe of Construction," *Physiol. Rev.*, 82, pp. 373-428 (2002).
Harman, D., "Aging: A Theory Based on Free Radical and Radiation Chemistry," *J. Gerontol.*, 11, pp. 298-300 (1992).
Petropoulos, I. et al., "Increase of Oxidatively Modified Protein Is Associated With a Decrease of Proteasome Activity and Content in Aging Epidermal Cells," *J. Gerontol. A. Biol. Sci.*, vol. 55A, No. 5, pp. B220-B227 (2000).

(Continued)

*Primary Examiner* — Julie Ha
*Assistant Examiner* — Li Ni Komatsu
(74) *Attorney, Agent, or Firm* — Thompson Hine L.L.P.

(57) ABSTRACT

The present invention concerns a peptidic hydrolyzate enriched in bioactive peptides, said hydrolyzate being a proteasome activator. Further, the present invention concerns a cosmetic or pharmaceutical composition comprising said hydrolyzate in a physiologically acceptable medium and also its use in treating signs of aging or photo-aging in skin and protecting the skin against challenges by ultraviolet radiation. Finally, the invention concerns a cosmetic treatment method intended to treat the signs of skin aging and photo-aging.

12 Claims, 2 Drawing Sheets

(56) References Cited

OTHER PUBLICATIONS

PCT, International Preliminary Report on Patentability, International Application No. PCT/FR2010/000324 (Nov. 1, 2011).

Bulteau, A-L. et al., "Forum Original Research Communication. Algae Extract-Mediated Stimulation and Protection of Proteasome Activity Within Human Keratinocytes Exposed to UVA and UVB Irradiation," *Antioxidants & Redox Signaling,* No. 8, Nos. 1 & 2, pp. 136-143 (2006).

Chondrogianni, N. et al., "Proteasome dysfunction in mammalian aging: Steps and factors involved," *Experimental Gerontology,* 40, pp. 931-938 (2005).

Harman, D., "Aging: A Theory Based on Free Radical and Radiation Chemistry," *J. Gerontol.,* 11 (3), pp. 298-300.

Kullmann, W., "Proteases as Catalysts for Enzymic Synthesis of Opioid Peptides," *The Journal of Biological Chemistry,* vol 255, No. 17, pp. 8234-8238 (Sep. 10, 1980).

\* cited by examiner

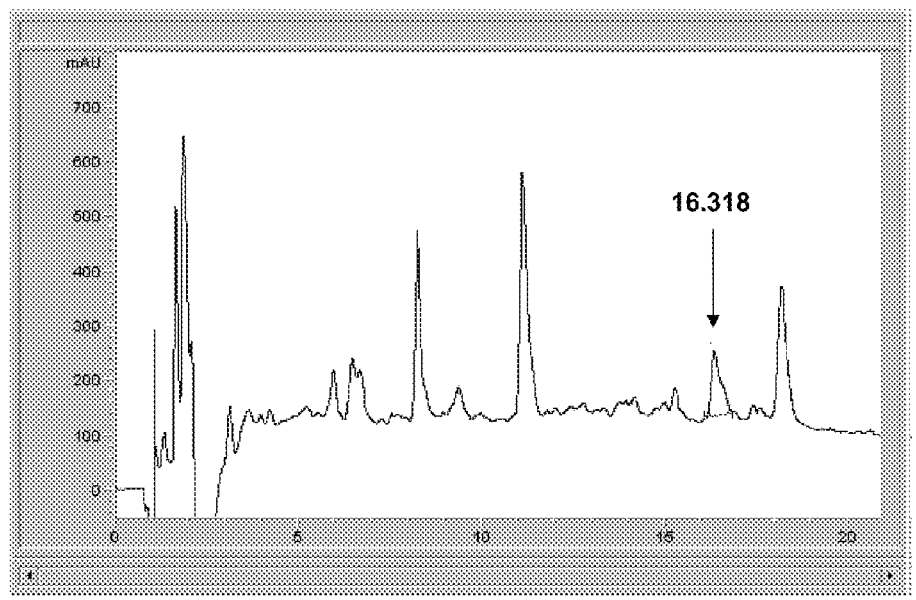
Figure 1 : HPLC chromatogram of a corn hydrolysate
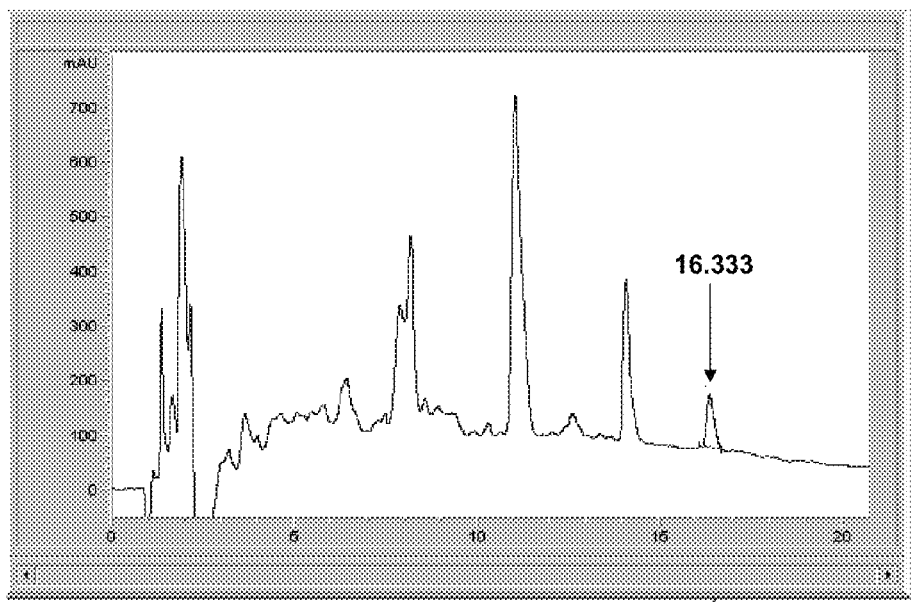
Figure 2 : HPLC chromatogram of a pea hydrolysate

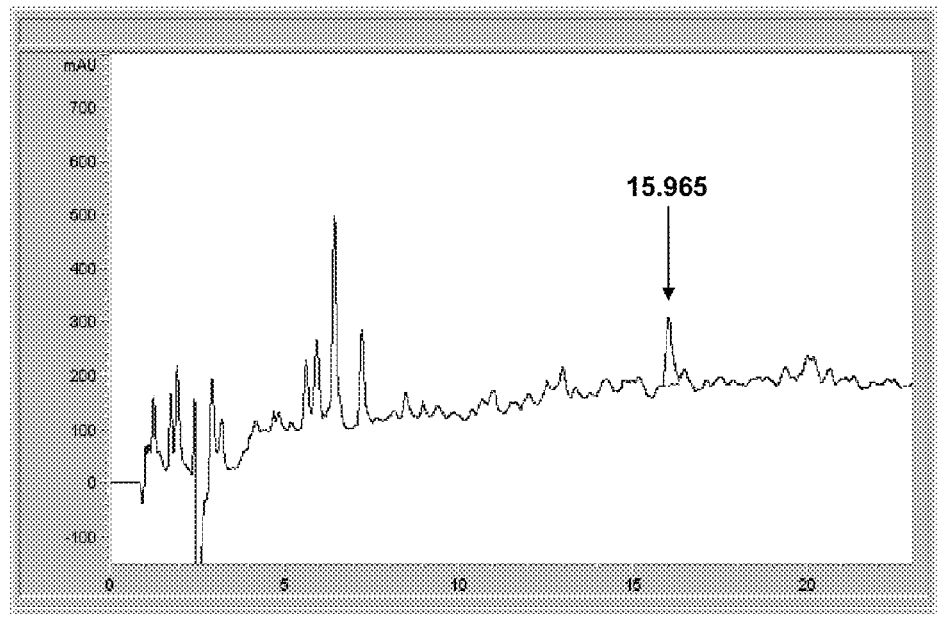
Figure 3 : HPLC chromatogram of a rice hydrolysate
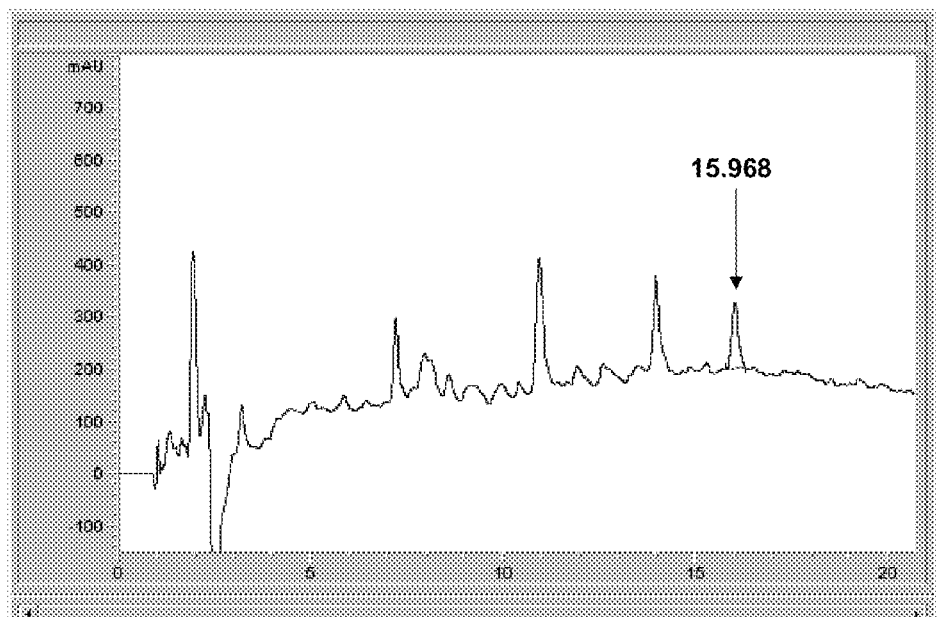
Figure 4 : HPLC chromatogram of a saccharomyces hydrolysate

SEQUENCE LISTING

```
<160> NUMBER OF SEQ ID NOS: 5

<210> SEQ ID NO 1
<211> LENGTH: 5
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 1
```

```
Arg Asp Cys Arg Arg
1               5

<210> SEQ ID NO 2
<211> LENGTH: 5
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 2

Asn Asp Cys Arg Lys
1               5

<210> SEQ ID NO 3
<211> LENGTH: 4
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 3

Asp Cys Arg His
1

<210> SEQ ID NO 4
<211> LENGTH: 4
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 4

Val Asp Cys Arg
1

<210> SEQ ID NO 5
<211> LENGTH: 3
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 5

Asp Cys Arg
1
```

PEPTIDIC HYDROLYZATE PROTEASOME ACTIVATORS AND COMPOSITIONS CONTAINING SAME

The present invention relates to the field of anti-aging active ingredients and to their uses, in particular in cosmetics. More particularly, the present invention relates to a peptidic hydrolyzate which is enriched in bioactive peptides, said hydrolyzate being a proteasome activator, and to its use in cosmetics and/or pharmaceuticals in order to prevent and/or correct the effects of aging and photo-aging of the skin, the nails and the hair, and to protect the skin against challenges due to UV radiation.

Aging corresponds to a series of physiological and psychological processes which modify the structure and functions of the organism from a certain age. Two types of aging can be distinguished: intrinsic aging on the one hand, and extrinsic aging on the other hand. Intrinsic aging is due to genetic factors, to biochemical modifications which take place when fatigued or stressed, or during the course of hormonal changes such as during pregnancy, etc. Extrinsic aging is due to environmental factors to which the organism is subjected throughout life, such as pollution, the sun, diseases, etc. It is a slow, progressive process which affects all of the organism's cells to different extents and manifests itself in different ways. As an example, the appearance of the skin is modified by various types of internal or external challenges; wrinkles and fine lines, hyper or hypo-pigmentation blemishes, dryness or even dehydration of the skin, thinning of the epidermis, elastosis, imperfections, age spots, etc, may thus appear. All of these changes affect not only the skin, but also the nails and the hair, such as the fingernails and the hair of the head. These modifications are due, inter alia, to an alteration in the functions of cell renewal, cell cohesion, collagen synthesis, elastin synthesis and the synthesis of other proteins and in the end result in a reduction in the protective barrier qualities of the skin and a less aesthetic appearance thereof. However, one of the principal processes responsible for aging of the cells is without doubt the accumulation of damaged proteins in those cells. In fact, the proteins are the target of various abnormal post-translational modifications such as oxidation, glycation, conjugation with substances derived from lipid peroxidation, or phenomena the incidence of which increase greatly with age.

It is known that free radicals play a key role in the aging process, and more particularly in the formation of oxidized, damaged proteins (Harman et al. "Aging: a theory based on free radical and radiation chemistry" *J. Gerontol.*, 11, 298-300). The accumulation of damaged proteins thus causes problems with the efficiency of the proteolytic systems in charge of eliminating those proteins, in particular that of the proteasomal system involved not only in the elimination of altered proteins, especially by oxidation, but also in the continuous renewal of intracellular proteins.

The ubiquitin-proteasome pathway plays a fundamental role in a vast number of biological processes. The degradation mechanisms of proteins by proteasome are in fact involved in major cellular mechanisms such as DNA repair, gene expression control, regulation of the cell cycle, controlling the quality of neo-synthesized proteins, apoptosis or the immune response (Glickman and Ciechanover, 2002).

The proteasome present in human cells is a very large multi-protein complex present in the cytoplasm and the nucleus. Purified forms of proteasome comprise two major subunits: a proteolytic core known as proteasome 20S, and a regulator complex, 19S, which binds to each of the two ends of proteasome 20S (Coux et al., 1996; Glickman and Coux, 2001). Proteasome 20S is a particle in the form of a hollow cylinder, composed of 28 alpha and beta subunits distributed in 4 heptameric rings. The peptidase activities are present on the inner surface of the cylinder and have an allosteric influence. Three proteolytic activities (trypsin-, chymotrypsin- and caspase-like) have been associated with proteasome 20S and together act to break down proteins into inactive peptides containing 3 to 20 amino acids. In addition to proteasome 20S, proteasome 26S comprises the 0.7 MDa regulator 19S complex constituted by approximately 20 subunits. Recent immunopurification studies have shown that other proteins may be associated with proteasome 20S and 19S (for example the regulator complex 11S).

Studies carried out in recent years have been able to correlate aging with proteasome activity. Although with age there is an increase in the accumulation of oxidized proteins, a reduction in the efficiency of the proteasomal system has been observed (Petropoulos et al., J. Gerontol. A. Biol. Sci. 2000, 55A:B220-7). This reduction in the efficiency of the proteasomal system is in fact due to a reduction in the quantity of proteasome. Those results have been confirmed by those from a study pertaining to the quantity and activity of proteasome in cells from centenarian individuals compared with young individuals (Chondrogianni et al., Exp. Gerontol. 2000; 35: 721-8). Those studies, as well as many others, clearly demonstrate the link between aging and proteasome activity and it may be assumed that inducing the expression of proteasome in cells of the skin or the nails or the hair could have a positive influence on aging or may even retard it.

With the aim of preventing or retarding aging, cosmetic compositions based on natural extracts have been proposed: an example is patent FR 2 822 701, which discloses a composition based on an extract from phaeodactylum algae to promote the proteasome activity. In addition, patent application FR 2 898 808 describes the use of a composition comprising an extract of micro-algae and arginine ferrulate, again to activate proteasome. Other compositions comprise chemical compounds which are capable of modulating the activity of proteasome in order to have an anti-aging effect. These compositions are described in patent applications WO 2006/105811 or WO 2005/061530. However, the peptide type compounds proposed are large, and it is difficult to use them as they are in the cosmetics field. Thus, there is a need, in particular in the cosmetics industry, for novel compositions deriving from natural extracts with active principles of smaller size which are effective as regards their use as a proteasome activator with an anti-aging effect.

Thus, the Applicant has discovered that a peptidic hydrolyzate which is enriched in bioactive peptides is capable of activating proteasome and could thus be useful in preventing and/or treating the signs of skin aging and photo-aging, as well as challenges due to UV radiation.

As a consequence, in a first aspect the present invention proposes a proteasome activator peptidic hydrolyzate, which is enriched in bioactive peptides, with a molecular weight of less than 6 kDa, containing 3 to 5 amino acids, each bioactive peptide comprising at least one aspartic acid residue, one cysteine residue and one arginine residue.

In a second aspect, the present invention proposes a cosmetic composition comprising said enriched peptidic hydrolyzate, as an active principle.

Further, in a third aspect, the present invention proposes the use of a cosmetic composition comprising said enriched peptidic hydrolyzate to prevent and/or treat the signs of skin aging and photo-aging and to ameliorate the degradation of damaged proteins by proteasome.

Finally, in a fourth aspect, the present invention proposes a method for the cosmetic treatment of the skin, the nails or the hair to be treated using the composition comprising said enriched peptidic hydrolyzate.

FIG. 1 represents an example of a chromatogram obtained by HPLC, identifying the peak corresponding to the bioactive peptide in a corn hydrolyzate.

FIG. 2 represents an example of a chromatogram obtained by HPLC, identifying the peak corresponding to the bioactive peptide in a pea hydrolyzate.

FIG. 3 represents an example of a chromatogram obtained by HPLC, identifying the peak corresponding to the bioactive peptide in a rice hydrolyzate.

FIG. 4 represents an example of a chromatogram obtained by HPLC, identifying the peak corresponding to the bioactive peptide in a Saccharomyces cerevisiae hydrolyzate.

In a first aspect, the present invention concerns a proteasome activator peptidic hydrolyzate, which is enriched in bioactive peptides, with a molecular weight of less than 6 kDa, containing 3 to 5 amino acids, each bioactive peptide comprising at least one aspartic acid residue, one cysteine residue and one arginine residue.

The term "peptidic hydrolyzate" means a mixture of compounds primarily represented by peptides or oligopeptides.

The term "bioactive peptides" means a protein fragment composed of a concatenation of at least 3 amino acids bonded together by modified or unmodified peptide linkages and which have activity as a proteasome activator. They are present in the proteins in the inactive form and become active after hydrolysis of those proteins.

Said enriched peptidic hydrolyzate of the invention is characterized in that it is a proteasome activator.

A peptidic hydrolyzate (and/or bioactive peptides) which is a "proteasome activator" denotes any peptidic hydrolyzate or biologically active peptide or derivative which is capable of augmenting the activity of the proteasome, either by increasing the protein synthesis of proteasome subunits (by direct or indirect modulation of genetic expression), or by other biological processes such as the stabilization of the subunits constituting the proteasome or the stabilization of messenger RNA transcripts.

The enriched peptidic hydrolyzate of the invention is characterized in that it can activate degradation of damaged proteins by proteasome. The term "damaged proteins" means proteins which have undergone oxidation due to reactive species of oxygen (free radicals), glycated proteins or proteins conjugated with substances derived from lipid peroxidation, etc.

Preferably, the peptidic hydrolyzate is enriched in bioactive peptides with general formula (I):

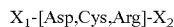

X$_1$-[Asp,Cys,Arg]-X$_2$ in which:
X$_1$ is an asparagine, a lysine, an aspartate, a valine, an arginine, or is absent;
X$_2$ is a histidine, a lysine, an arginine, or is absent.

Preferably, the peptidic hydrolyzate is rich in bioactive peptides with the following formula:

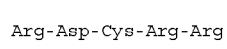

Arg-Asp-Cys-Arg-Arg (SEQ ID No. 1)

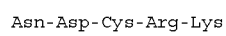

Asn-Asp-Cys-Arg-Lys (SEQ ID No. 2)

Asp-Cys-Arg-His (SEQ ID No. 3)

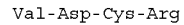

Val-Asp-Cys-Arg (SEQ ID No. 4)

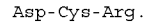

Asp-Cys-Arg. (SEQ ID No. 5)

These peptides have been identified as being particularly active as proteasome activators and thus are of particular interest as an anti-aging agent.

The enriched peptidic hydrolyzate of the invention may be obtained from various sources of proteins, irrespective of their animal or vegetable origin. In a first embodiment, the enriched peptidic hydrolyzate is derived from the hydrolysis of plants selected from corn (*Zea mayz* L.), pea (*Pisum sativum*) or rice (*Oryza sativa* L.). Preferably, the plants used do not undergo prior fermentation. In a second embodiment, the enriched peptidic hydrolyzate is derived from the hydrolysis of yeasts from the genus *Saccharomyces*, and more particularly from the species *Saccharomyces cerevisiae*.

Thus, the invention may be carried out using seeds from one of numerous plants from the genus *Zea*, preferably from the species *Zea mayz* L. In accordance with the invention, the plant material used will be the seed, preferably the seed freed from its envelope by means of a hulling step.

The invention may also be carried out using one of the many plants from the pea family (Fabaceaea). As an example, plants from the pea species *Pisum sativum* L. may be used. The term "pea" also denotes the seed, which itself is rich in proteins (25%).

Plants from the rice family (Poaceae), in particular those from the genus *Oryza* and more preferably the species *Oryza sativa* L., may be used to produce the hydrolyzate of the invention. The plant material used will be the seed, preferably the seed freed from its envelope by a hulling step.

Finally, the invention may also be carried out using yeasts from the genus *Saccharomyces*, preferably yeasts from the species *Saccharomyces cerevisiae*.

Any method for extraction or purification which is known to the skilled person may be used in order to prepare the hydrolyzate of the invention.

In a first step, seeds or a specific portion of the plant (leaves, tubers, roots, etc) are milled using a plant mill. The powder obtained may subsequently be "delipidized" using a conventional organic solvent (for example an alcohol, hexane or acetone).

With yeasts, in a first step they are cultured in a conventional manner in a medium which is suitable for their development, preferably in the presence of lactose. They are harvested by centrifuging then taken up in suspension in a buffer solution, preferably a phosphate buffer. In a second step, those cells are ruptured using a French press or a ball mill; the majority of the insoluble membrane components are removed by centrifuging or filtering.

Next, proteins are extracted using a modified conventional method (Osborne, 1924); the milled plant or yeast lysate is taken up in suspension in an alkaline solution containing an adsorbent product of the insoluble polyvinylpolypyrrolidone (PVPP) type (0.01-20%); it has been observed that the hydrolysis operations and subsequent purification operations have been facilitated by this means. In particular, the concentrations of phenol type substances, which interact with the proteins, are substantially reduced.

The soluble fraction containing proteins, glucides and possibly lipids is recovered after the centrifuging and filtration steps. That crude solution is then hydrolysed under managed conditions to generate soluble peptides. Hydrolysis is defined as a chemical reaction involving cleavage of a molecule by water, that reaction possibly being carried out in a neutral, acidic or basic medium. In accordance with the invention, the hydrolysis is carried out chemically and/or advantageously using proteolytic enzymes. It is also possible to cite the use of endoproteases of plant origin (papain, bromain, ficain) and from micro-organisms (*Aspergillus, Rhizopus, Bacillus*, etc). The hydrolysis conditions are selected in order to promote enrichment in bioactive peptides.

For the same reasons as before, i.e. the elimination of polyphenolic substances, a quantity of polyvinylpolypyrrolidone is added to the reaction medium during this managed hydrolysis step. After filtration to eliminate the enzymes and polymers, a first filtrate is obtained.

The hydrolyzate obtained at this stage may be purified further in order to select the low molecular weight fractions, preferably less than 6 kDa, and the peptides generated as a function of their nature. Purification may advantageously be carried out by successive ultrafiltration steps through filters with decreasing porosities, retaining the filtrates at each step, and/or by a method of the chromatographic type, in order to specifically enrich the hydrolyzate in bioactive peptides.

Next, a phase for dilution in water or in any mixture containing water is carried out, followed by sterilization by ultrafiltration in order to obtain an enriched peptidic hydrolyzate characterized by a protein content of 0.5 to 5.5 g/l. This enriched peptidic hydrolyzate corresponds to the most purified form of the active principle of the invention.

The peptidic hydrolyzate obtained in accordance with the invention is analysed qualitatively and quantitatively using high pressure liquid chromatography (HPLC), which can analyse proteins with molecular weights of 0.2 to 2.5 kDa (using an appropriate solvent gradient). The various peptide fractions which are able to be isolated are then analysed for their biological efficacy. These various fractions are then analysed by mass spectrometry in order to specifically identify the amino acid content of the peptides of each peak. A sequencing analysis is also carried out in order to determine the peptide sequence of the bioactive peptides.

Finally, the enriched peptidic hydrolyzate obtained is composed of peptides with a molecular weight of less than 6 kDa and is enriched in bioactive peptide containing 3 to 5 amino acids comprising at least one aspartic acid residue, one cysteine residue and one arginine residue.

This peptidic hydrolyzate of the invention, enriched in bioactive peptides, may also be used as a drug.

In a second aspect, the present invention concerns a cosmetic composition comprising the peptidic hydrolyzate enriched in bioactive peptides as described above as the active principle.

Preferably, the compositions of the invention are in a form suitable for topical application comprising a cosmetically acceptable medium. The term "cosmetically acceptable" means media which are suitable for use in contact with human skin or the nails or the hair, with no risk of toxicity, incompatibility, instability, allergic response or the like. Preferably, said peptidic hydrolyzate is present in the composition in a quantity representing 0.0001% to 20% of the total composition weight, preferably in a quantity representing 0.05% to 5% of the total composition weight.

In the compositions of the invention, the peptidic hydrolyzate enriched in bioactive peptides is dissolved in one or more solvents such as water, glycerol, ethanol, propylene glycol, butylene glycol, dipropylene glycol, ethoxylated or propoxylated diglycols, cyclic polyols, vaseline, a vegetable oil or any mixture of these solvents.

According to another advantageous embodiment, the peptidic hydrolyzate of the invention is dissolved in a cosmetic or pharmaceutical vector such as liposomes or adsorbed onto powdered organic polymers, mineral supports such as talcs or bentonites, and more generally dissolved in or fixed onto any physiologically acceptable vector.

The compositions intended for application to the skin may be in the form of an aqueous or hydro-alcoholic solution, a water-in-oil or oil-in-water emulsion, a microemulsion, an aqueous or anhydrous gel, a serum or a dispersion of vesicles, a patch, a cream, a spray, an ointment, a pomade, a lotion, a colloid, a solution, a suspension or other. The compositions may also be applied to the nails and the hair in the form of a shampoo, dye or mascara for application using a brush or comb, in particular to the eyelashes, eyelids or hair, or toiletries for the nails such as a nail polish.

In a particular embodiment, the composition of the invention further contains at least one other active principle promoting the action of said enriched peptidic hydrolyzate. Non-limiting examples of classes of ingredients which may be cited are as follows: peptide active agents, other plant extracts, healing agents, anti-aging agents, anti-wrinkle agents, soothing agents, free radical scavengers, UV screens, agents stimulating the synthesis of dermal macromolecules or energy metabolism, moisturizers, antibacterial agents, antifungal agents, anti-inflammatory agents, anaesthetics, agents modulating skin differentiation or pigmentation or skin depigmentation, and agents stimulating the growth of the nails or hair, etc. Preferably, an agent with anti-wrinkle activity is used, such as a free radical scavenger or antioxidant, or an agent stimulating the synthesis of dermal macromolecules, or an agent stimulating energy metabolism. More particularly, the active principle is selected from vitamins, phytosterols, flavonoids, DHEA and/or one of its precursors or chemical or biological derivatives, a metalloproteinase inhibitor, or a retinoid. Furthermore, additives such as thickening agents, emulsifiers, wetting agents, emollients, fragrances, antioxidants, film-forming agents, chelating agents, sequestrating agents, packaging agents, etc may be added to the composition.

In all cases, the skilled person will ensure that these adjuvants as well as their proportions are selected so that they do not have a deleterious effect on the desired advantageous properties of the composition of the invention. These adjuvants may, for example, be present in concentrations of 0.01% to 20% of the total composition weight. When the composition of the invention is an emulsion, the fatty phase may represent 5% to 80% by weight, preferably 5% to 50% by weight with respect to the total composition weight. The emulsifiers and co-emulsifiers used in the composition will be selected from those in conventional use in the field under consideration. As an example, they may be used in a proportion of 0.3% to 30% by weight, with respect to the total composition weight.

Finally, the invention pertains to a composition comprising said peptidic hydrolyzate in order to increase the activity of proteasome and to improve the degradation of damaged proteins by the proteasome.

In a third aspect, the invention concerns the use of a cosmetic composition comprising said enriched peptidic hydrolyzate and a cosmetically acceptable medium to prevent and/or treat the signs of skin aging and photo-aging.

The "signs of skin aging" include but are not limited to any manifestation which is visible on the skin caused by aging. This in particular means wrinkles, deep and coarse wrinkles, fine lines, cracks, slackening of cutaneous and sub-cutaneous tissues, the loss of skin elasticity and atony, loss of firmness and skin tonicity, and dermal atrophy. Furthermore, the term "signs of skin aging" means enlarged pores, imperfections, discoloration, age spots, keratosis, loss of collagen, and other changes in the dermis and epidermis, but also any modification to the external appearance of the skin, the nails and the hair due to aging such as, for example, superficial roughness of the stratum corneum, but also any internal modification to the skin which does not systematically result in a modified external appearance, such as thinning of the skin. The term "photo-aging" means premature aging of the skin caused by cumulative prolonged exposure to the sun.

Thus, the present invention pertains to the use of a composition to treat or prevent wrinkles, deep and coarse wrinkles, fine lines, cracks, slackening of cutaneous and sub-cutaneous tissues, the loss of skin elasticity and atony, loss of firmness and skin tonicity, and dermal atrophy.

In a further aspect, the invention concerns the use of a composition of the invention to protect the skin against challenges due to UV radiation.

Finally, the invention pertains to the use of a composition comprising a peptidic hydrolyzate to increase the activity of proteasome and to improve the degradation of damaged proteins by proteasome.

Finally, the present invention pertains to a cosmetic treatment method consisting of topical application of a composition comprising an effective quantity of enriched peptidic hydrolyzate in accordance with the invention to the skin, to prevent and/or treat signs of skin aging or photo-aging. Furthermore, this cosmetic treatment method may be applied before going to bed in order to clean the skin cells during the cell renewal cycle. In fact, during the night, the skin prioritizes renewal functions as well as metabolic synthesis processes. As a result, applying the composition as claimed in a manner that respects the biological rhythm of the skin means that a rejuvenating and regenerative effect can be obtained, which stimulates cell renewal.

The following examples describe and demonstrate the effective nature of the peptide compounds as described in accordance with the invention but should not be interpreted as limiting the scope of the present invention.

EXAMPLE 1

Preparation of a Peptidic Hydrolyzate from Corn Meal (*Zea Mays* L.)

Corn meal (*Zea mays* L.) was dissolved in 10 volumes of water in the presence of 2% of POLYCLAR® 10 polyvinylpyrrolidone (polyvinylpyrrolidone—PVPP—insoluble). The mixture was adjusted to a pH in the range 6 to 8 with an aqueous 1M solution of sodium hydroxide.

After adjusting the pH, 2% papain was added to the reaction medium. Hydrolysis was complete after 2 hours mixing at 55° C. Next, the enzyme was inactivated by heating the solution at 80° C. for 2 hours. After centrifuging, the supernatant aqueous solution corresponding to a crude corn hydrolyzate was recovered. The specific conditions for hydrolysis were selected so as to allow an enrichment in bioactive peptides containing 3 to 5 amino acids comprising at least one aspartic acid residue, one cysteine residue and one arginine residue.

The method for the purification of the crude hydrolyzate commenced with successive filtrations using Seitz-Orion filter plates with decreasing porosity (to 0.2 μm) in order to obtain a bright, clear yellow solution termed hydrolyzate 1.

In this step, the corn hydrolyzate 1 was characterized by a dry extract assaying at 20 to 30 g/kg, a protein content of 20 to 25 g/l and a sugar content of 2 to 5 g/l.

The protein nature of hydrolyzate 1 was identified after electrophoretic analysis on NUPAGE® Bis-Tris Pre-cast polyacrylamide gel (Invitrogen). The corn protein hydrolyzate was heated to 70° C. for 10 minutes under reducing denaturing conditions in a NUPAGE® LDS sample preparation buffer. Protein migration was carried out in a NUPAGE® MES migration buffer with the SeeBlue Plus2 standard as a molecular weight marker. Protein staining was carried out using COOMASSIE BLUE® R-250 dye. Under these conditions, it was observed that the proteins obtained had a molecular weight of less than 6 kDa.

Hydrolyzate 1 was then purified by ultrafiltration with a PELLICON® 2 Biomax 5 kDa cassette to eliminate high molecular weight proteins and retain only compounds of a peptide nature that were less than 5 kDa.

After this final purification, a dilution phase was carried out to obtain a peptidic hydrolyzate characterized by a protein content in the range 3.5 to 5.5 g/l. This peptidic hydrolyzate corresponded to the active principle of the invention.

This peptidic hydrolyzate was then analysed using high pressure liquid chromatography (HPLC) with the aid of a HP 1100 apparatus controlled using ChemStation software. The column used during elution of the hydrolyzate was a NUCLEOSIL® 300-5 C4MPN (125×4 nm) column which allowed proteins with molecular weights of 0.2 to 25 kDa to be chromatographed under the following conditions:
methanol gradient
Uptisphere OPB 125×3 mm column
solvent A: HPLC grade water containing 0.1% heptafluorobutyric acid (HFBA)
solvent B: HPLC grade methanol containing 0.1% heptafluorobutyric acid (HFBA)
gradient: 100% to 15% solvent A in 35 min.

An example of a chromatogram obtained by HPLC (high pressure liquid chromatography) identifying a peak corresponding to the bioactive peptides is given in FIG. 1.

These various fractions were then analysed by mass spectrometry in order to specifically identify the amino acid content of the peptides of each peak. Sequencing analysis was also carried out in order to determine the peptide sequence of the bioactive peptide.

EXAMPLE 2

Preparation of a Peptidic Hydrolyzate Enriched in Bioactive Peptides from Peas (*Pisum Sativum* L.)

The peptidic hydrolyzate was obtained from an extract from plants of the species *Pisum sativum* L. Clearly, the extract could have been prepared from plants from at least any one of the many varieties and species belonging to the genus Pisum.

In a first step, 1 kg of shelled peas were delipidized by the action of an organic solvent: hexane.

The pea flour thus obtained was dissolved in 10 volumes of water in the presence of 2% of POLYCLAR® 10 polyvinylpyrrolidone (polyvinylpyrrolidone—PVPP —insoluble). The mixture was adjusted to a pH in the range 6 to 7 with an aqueous 1M solution of sodium hydroxide.

After adjusting the pH, 2% FLAVOURZYM® aminopeptidase was added to the reaction medium. Hydrolysis was complete after 2 hours mixing at 50° C. Next, the enzyme was inactivated by heating the solution to 80° C. for 2 hours. The reaction mixture obtained thereby corresponded to the pea extract. The specific conditions for hydrolysis were selected so as to allow an enrichment in bioactive peptides containing 3 to 5 amino acids comprising at least one aspartic acid residue, one cysteine residue and one arginine residue.

The purification method commenced with successive filtrations using Seitz-Orion filter plates with decreasing porosity (to 0.2 μm) in order to obtain a bright, clear solution. In this step, the pea hydrolyzate was characterized by a dry extract assaying at 70-80 g/kg, a protein content of 55-65 g/l, a sugar content of 2-5 g/l and a polyphenol content of 1-3 g/l.

The protein nature of this hydrolyzate was identified by polyacrylamide gel electrophoresis. For this analysis, NUPAGE® Bis-Tris Pre-cast gels (Invitrogen) were used. The pea protein hydrolyzate was heated to 70° C. for 10 minutes under reducing denaturing conditions in a NUPAGE® LDS sample preparation buffer. Protein migration was carried out in a NUPAGE® MES migration buffer with the SeeBlue Plus2 standard as a molecular weight marker. Protein staining was carried out using COOMASSIE BLUE® R-250 dye. Under these conditions, 2 major families of proteins were observed: a first family corresponding to proteins with a molecular weight of 20 to 25 kDa and the last family with proteins with molecular weights of less than 5 kDa.

This solution was then purified to eliminate proteins with molecular weights of more than 5 kDa using tangential flow filtration. To this end, the pea hydrolyzate was pumped under pressure through a PELLICON® support provided with a PELLICON® 2 Biomax 30 kDa cassette. This first filtrate was recovered for subsequent filtration through another PELLICON® 2 Biomax 5 kDa cassette. After this purification, a bright, clear yellow-beige peptidic hydrolyzate was obtained. It was characterized by a dry extract in the range 50 to 55 g/kg and a protein content in the range 50 to 52 g/l.

This solution was then analysed using high pressure liquid chromatography (HPLC) with the aid of a HP 1100 apparatus controlled using ChemStation software. The column used during elution of the pea extract was a NUCLEOSIL® 300-5 C4MPN (125×4 nm) column. This column enabled proteins with molecular weights of 0.2 to 25 kDa to be chromatographed (using a suitable solvent gradient identical to Example 1). Under these chromatographic conditions, several peptide fractions were able to be isolated.

These various fractions were then analysed by mass spectrometry in order to specifically identify the amino acid content of the peptides of each peak. Sequencing analysis was also carried out in order to determine the peptide sequence of the bioactive peptides. An example of a chromatogram obtained by HPLC (high pressure liquid chromatography) identifying a peak corresponding to the bioactive peptides is given in FIG. 2.

The amino acid composition of the active principle of the invention was also determined. It was carried out after acid hydrolysis and identification by high pressure liquid chromatography using PICT (phenylisothiocyanate) pre-column derivatization.

EXAMPLE 3

Preparation of a Peptidic Hydrolyzate Enriched in Bioactive Peptides from *Saccharomyces Cerevisiae* Yeasts The peptidic hydrolyzate could be obtained from an extract from yeasts of the species *Saccharomyces cerevisiae*. The yeasts were cultivated in a medium suitable for their development, preferably in the presence of lactose, then centrifuged to recover a biomass. The *Saccharomyces* biomass was dissolved in 10 volumes of water in the presence of 2% of POLYCLAR® 10 polyvinylpyrrolidone (polyvinylpyrrolidone—PVPP —insoluble) and 0.2% of activated charcoal. The mixture was adjusted to a pH in the range 6 to 7.5 with an aqueous 1M solution of sodium hydroxide.

After adjusting the pH, 2% papain was added to the reaction medium. Hydrolysis was complete after 2 hours mixing at 55° C. Next, the enzyme was inactivated by heating the solution to 80° C. for 2 hours. After centrifuging, the reaction mixture corresponding to the *saccharomyces* extract was obtained. The specific conditions for hydrolysis were selected so as to allow an enrichment in bioactive peptides containing 3 to 5 amino acids comprising at least one aspartic acid residue, one cysteine residue and one arginine residue.

The purification method commenced with successive filtrations using Seitz-Orion filter plates with decreasing porosity (to 0.2 μm) in order to obtain a bright, clear solution In this step, the Saccharomyces extract was characterized by a dry extract of 25 to 35 g/kg, a protein content of 10 to 15 g/l and a sugar content of 5-10 g/l.

The protein nature of this extract was identified by polyacrylamide gel electrophoresis. For this analysis, NUPAGE® Bis-Tris Pre-cast gels (Invitrogen) were used. The peptidic hydrolyzate was heated to 70° C. for 10 minutes under reducing denaturing conditions in a NUPAGE® LDS sample preparation buffer. A solution of NUPAGE® antioxidizing agent was added to the internal cell (cathode) to prevent the reduced proteins from re-oxidizing during electrophoresis. Protein migration was carried out in a NUPAGE® MES migration buffer with the SeeBlue Plus2 standard as a molecular weight marker. Protein staining was carried out using COOMASSIE BLUE® R-250 dye. Under these conditions, 3 major families of proteins were observed: the first family corresponded to proteins with a molecular weight of more than 75 kDa, the second family of protein of 20 to 25 kDa and the last family with proteins with molecular weights of less than 5 kDa.

This solution was then purified to eliminate proteins with molecular weights of more than 5 kDa using tangential flow filtration. To this end, the pea hydrolyzate was pumped under pressure through a PELLICON® support provided with a PELLICON® 2 Biomax 50 kDa cassette. This first filtrate was recovered for subsequent filtration through another PELLICON® 2 Biomax 10 kDa cassette. A second filtrate was then recovered which was eluted again through a final PELLICON® 2 Biomax 5 kDa cassette. After this purification, a bright, clear beige *Saccharomyces* plant extract was obtained. It was characterized by a dry extract in the range 35 to 45 g/kg and a protein content of 30 to 40 g/l.

This solution was then analysed using high pressure liquid chromatography with the aid of a HP 1100 apparatus controlled using ChemStation software. The column used during elution of the Saccharomyces hydrolyzate was a NUCLEOSIL® 300-5 C4MPN (125×4 nm) column. This column enabled proteins with molecular weights of 0.2 to 25 kDa to be chromatographed (using an appropriate gradient identical to that of Example 1). Under these chromatographic conditions, several peptide fractions were able to be isolated.

These various fractions were then analysed by mass spectrometry in order to specifically identify the amino acid content of the peptides of each peak. Sequencing analysis was also carried out in order to determine the peptide sequence of the bioactive peptides. An example of a chromatogram obtained by HPLC (high pressure liquid chromatography) identifying a peak corresponding to the bioactive peptides is given in FIG. 4.

The amino acid composition of the active principle of the invention was also determined. It was carried out after acid hydrolysis and identification by high pressure liquid chromatography using PICT (phenylisothiocyanate) pre-column derivatization

EXAMPLE 4

Identification of the Activator Effect of Corn Peptidic Hydrolyzate in Accordance with Example 1 on the Enzymatic Activity of Proteasome 20S on Aged Keratinocytes Under Culture Experimentally aged keratinocytes which had been cultured for 15 days were treated with 1% of our peptidic hydrolyzate from corn as produced in accordance with Example 1. Next, the enzymatic activities of proteasome 20S was studied. Proteasome 20S is the subunit responsible for enzymatic hydrolyzate. Three enzymatic activities could be studied: the trypsin-like, chymotrypsin-like and peptidylglutamyl-peptide hydrolase (PGPH) activity. We proposed a study of these activities by means of an enzymatic assay specific for each activity.
Protocol The aged keratinocytes were cultured for 15 days. The cells were treated by adding a 1% solution of our peptidic hydrolyzate directly to the medium, which was renewed 3 times per week throughout the experiment.

Each activity was assayed using specific substrates labelled with a fluorescent compound: 7-amido-4-methyl-coumarine (AMC). After cleavage, the fluoresecence of the AMC, which has an excitation wavelength of 350 nm, was read at 440 nm. The fluoresecence intensity is proportional to the quantity of fluorochrome obtained and as a result, this quantity is proportional to the quantity of substrate hydrolyzed.

The synthetic peptide Boc-Leu-Arg-Arg-AMC is specific for trypsin activity.

The synthetic peptide Suc-Leu-Leu-Val-Try-AMC is specific for chymotrypsin activity.

The synthetic peptide Z-Leu-Leu-Glu-AMC is specific for peptidylglutamyl-peptide hydrolase activity.

These peptides were supplied and labelled by SIGMA ALDRICH, Saint-Louis, Mo., USA.

The cells were detached from the support in an extraction buffer. Next, they were sonicated for 1 minute at 4° C. then centrifuged at 15000 g for 30 minutes at 4° C. The protein assay was carried out using the BCA kit (Pierce). After incubating the cell lysate with the specific synthetic substrate for the activity being studied, the fluorescence was read at 440 nm using a Synergy spectrophotometer (BIOTEK, Vermont, USA).
Results We observed that for the 3 activities being studied, the peptidic hydrolyzate of Example 1 could increase the enzymatic activity of proteasome 20S. The trypsin-like activity was increased by 155.3% during treatment with the active ingredient; the chymotrypsin-like activity was increased by 130%, and an increase of 144.6% was recorded for the peptidylglutamyl-peptide hydrolase activity.
Conclusions The peptidic hydrolyzate enriched with bioactive peptides of Example 1, used in a concentration of 1% on experimentally aged keratinocytes under culture, could increase the specific enzymatic activities of proteasome 20S.

The experiment was carried out several times and a statistical test (Student t-test) could be carried out. The increase in the activities was significant for the study of the trypsin-like, chymotrypsin-like activity ($p=0.033$ and $p=0.0477$ respectively), and highly significant for the peptidylglutamyl-peptide hydrolase activity ($p=0.00053$).

EXAMPLE 5

Identification of the Anti-Aging Effect of the Yeast Peptidic Hydrolyzate of Example 3 on Aged Keratinocytes Under Culture A study of the anti-aging effect of yeast peptidic hydrolyzate was studied by evaluating the expression of beta-galactosidase protein on experimentally aged keratinocytes under culture. Beta-galactosidase activity is known to be present in senescent cells, while no beta-galactosidase activity is found in pre-senescent, quiescent or immortal cells.
Protocol Experimentally aged keratinocytes in 8-well Labtec plates were cultured and kept for 20 days in the presence or absence of 1% yeast peptidic hydrolyzate enriched in bioactive peptides. The treatment was carried out 3 times per week by direct addition to the medium.

Untreated cells were cultured for the same experimental period and acted as a control. On the day of labelling, the cells were washed, and fixed in a 2% glutaraldehyde—2% formaldehyde mixture for 3 minutes. The cells were then washed and 300 µl of 5-bromo-4-chloro-3 indolyl-D-galactosidase, generally known as X-gal (beta-galactosidase substrate) was applied. Incubation was carried out for 24 hours in the $CO_2$ incubator, then the cells were washed and the Labtec plate was rapidly installed in a suitable medium. The observation was carried out using a transmission microscope. The principle was simple: when the cells are senescent and contain beta-galactosidase, the X-gal substrate is cleaved into an insoluble blue substance. The beta-galactosidase activity was revealed by blue staining of the cells. The deeper the blue of the cells, the larger the number of senescent cells.
Results/Conclusions:

We can see that in the presence of the active ingredient, i.e. the yeast peptidic hydrolyzate, the beta-galactosidase activity is substantially reduced in treated cells compared with untreated cells.

As a consequence, the peptidic hydrolyzate of the invention has an anti-aging effect on experimentally aged keratinocytes cultured for 20 days.

EXAMPLE 6

Evaluation of Carbonylation of Proteins on Fibroblasts Treated with Rice Peptidic Hydrolyzate and Subjected to Ultraviolet Radiation (UVB)

Protocol:

Cultured normal human fibroblasts were seeded into 100 diameter dishes. When the cells reached 70% confluence, the cells were treated for 48 hours with a rice peptidic hydrolyzate enriched in bioactive peptides diluted to a concentration of 1% in the medium. The cells underwent UVB irradiation at 100 $mJ/cm^2$, then were placed in the presence of the active principle for a further 48 hours. Control dishes with cells not treated with the active principle but irradiated acted as the control. The cells were washed then detached from the support using a suitable extraction buffer. The extracted proteins were centrifuged at 4° C. at 10000 rpm for 10 minutes before being assayed using the PCA protein kit (Pierce). Protein carbonylation was carried out using a test based on the immunodetection of carbonylated groups which had been derivatized with 2,4-dinitrophenylhydrazine (DNP) (SIGMA) in accordance with the reaction:

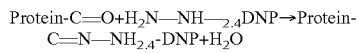

Protein-C=O+H$_2$N—NH—$_{2,4}$DNP→Protein-C=N—NH$_{2,4}$-DNP+H$_2$O

In brief, 15 μl of the sample was reacted with 45 μl of DNP for 45 minutes at ambient temperature. Next, 5 μl of the mixture was diluted in 1 ml of phosphate buffer saline and 200 μl of this dilution was placed in a 96 well plate overnight at 4° C. in the presence of 150 μl of BSA (fraction V).

After washing three times in phosphate buffer saline (PBS), rabbit anti-dinitrophenyl biotinylated antibody (CAL-BIOCHEM) was diluted to $\frac{1}{5000}^{th}$ in 0.1% serum albumin buffer in the presence of 0.1% of Tween 20 and incubated in microplates for 1 hour at 37° C. After 3 washes, the streptavidin-peroxidase (DAKO) complex diluted to $\frac{1}{3000}^{th}$ was incubated in 0.1% serum albumin buffer in the presence of 0.1% Tween 20 and incubated in the microplates for 1 hour at ambient temperature. After 3 washes, it was revealed using 200 μl of tetramethylbenzidine (TMB, SIGMA) for 25 minutes at ambient temperature. Next, adding 100 μl of 2.5M sulphuric acid stopped the reaction. The OD was read at 490 nm. In order to convert the OD obtained into the number of carbonyl groups present in the samples, a calibration curve was drawn up by varying the proportions of oxidized BSA from 0 to 100%.

Results:

In the presence of UVB, the untreated cells were strongly carbonylated and increased by 110% compared with the non-irradiated and untreated cells. In the presence of rice peptidic hydrolyzate enriched by 1% in bioactive peptides, the degree of carbonylation was reduced by 34%. The experiment was carried out several times and a statistical test (Student-t test) was able to be carried out. The reduction in carbonylation was significant and p=0.0298.

In conclusion, the active principle of the invention can be used to protect cells against the deleterious effects of UV, i.e. against its oxidizing effects. The rice peptidic hydrolyzate can be used to reduce protein oxidation by more than 34%.

EXAMPLE 7

Clinical Test

Protocol for Clinical Evaluation

Either a placebo or a yeast peptidic hydrolyzate enriched in bioactive peptides in accordance with Example 3 were applied to 12 volunteers aged from 29 to 56 years twice a day, morning and evening, in a dose of 2 mg/cm$^2$ over 24 hours. A clinical evaluation of the results allowed several wrinkle and fine line parameters to be measured.

The measurement of wrinkles and fine lines was carried out using QUANTIRIDE, which is an evaluation method that can measure the number, length and depth of wrinkles by producing a replica of the skin before and after treatment, using a silicone polymer.

The results are summarized in the tables below:

Wrinkle Quantification Results

| Wrinkle length | Time | Measurement (mm) | Wilcoxon | % of volunteers with improvement |
|---|---|---|---|---|
| Hydrolyzate | J 23-J 0 | −0.104 | 0.017 | 83.3% |
| Placebo | J 23-J 0 | 0.0029 | N/A | N/A |

| Number of wrinkles | Time | Measurement (mm) | Wilcoxon | % of volunteers with improvement |
|---|---|---|---|---|
| Hydrolyzate | J 23-J 0 | −9.5833 | 0.0249* | 75% |
| Placebo | J 23-J 0 | 5.8333 | N/A | N/A |

| Wrinkle depth | Time | Measurement (mm) | Wilcoxon | % of volunteers with improvement |
|---|---|---|---|---|
| Hydrolyzate | J 23-J 0 | −6.5557 | 0.0075 | 75% |
| Placebo | J 23-J 0 | 3.6284 | N/A | N/A |

Conclusions:

After 24 days of treatment, we observed a statistical reduction in the total length of wrinkles in 83.3% of treated subjects, as well as a reduction in the number of wrinkles in 75% of treated subjects. Regarding wrinkle length, a significant difference was observed between the yeast peptidic hydrolyzate enriched with bioactive peptides and the placebo (p=0.017). Regarding the wrinkle depth, the difference between the active principle and the placebo was also significant (p=0.0075) and was observed in 75% of the volunteers.

Applicants incorporate by reference the material contained in the accompanying computer readable Sequence Listing entitled "US09-126SequenceListing.txt", which was created on Jan. 3, 2012, and is 1,546 bytes in size, and hereby confirm that the information recorded in the computer readable form is identical to the written sequence listing.

The invention claimed is:

1. A method for treating the signs of skin aging and photo-aging or treating against photo-aging, the method comprising:

providing a proteasome activating peptidic hydrolyzate from corn, pea, yeast or rice comprising bioactive peptides, with a molecular weight of less than 6 kDa, comprising from 3 to 5 amino acids, each bioactive peptide comprising at least one aspartic acid, one cysteine residue, and an arginine residue, wherein the bioactive peptide is selected from the group consisting of:

Arg-Asp-Cys-Arg-Arg, (SEQ ID No. 1)

Asn-Asp-Cys-Arg-Lys, (SEQ ID No. 2)

Asp-Cys-Arg-His, (SEQ ID No. 3)

Val-Asp-Cys-Arg, (SEQ ID No. 4)

and

-continued

Asp-Cys-Arg; (SEQ ID No. 5)

topically applying an effective quantity of said peptidic hydrolyzate to the skin, the nails or the hair to be treated.

2. The method according to claim 1, wherein providing the proteasome activating peptidic hydrolyzate in a cosmetic composition.

3. The method according to claim 2, wherein said cosmetic composition comprises a cosmetically acceptable medium.

4. The method of claim 2, wherein said peptidic hydrolyzate is present in the cosmetic composition in a quantity from 0.0001% to 20% of the total weight of the composition.

5. The method of claim 2, wherein the peptidic hydrolyzate is present in the cosmetic composition in a quantity from 0.05% to 5% of the total weight of the composition.

6. The method of claim 2, wherein the cosmetic composition further comprises one or more solvents selected from the group consisting of water, glycerol, ethanol, propylene glycol, butylene glycol, dipropylene glycol, ethoxylated or propoxylated diglycols, cyclic polyols, white petroleum jelly, a vegetable oil, and combinations thereof, said peptidic hydrolyzate being dissolved therein.

7. The method of claim 2, wherein the cosmetic composition further comprises at least one active principle promoting the action of said peptidic hydrolyzate selected from the group consisting of a free radical scavenger, an antioxidant, vitamins, phytosterols, flavonoids, dehydroepiandrosterone (DHEA), a metalloproteinase inhibitor, or a retinoid.

8. The method of claim 1, further comprising isolating said peptidic hydrolyzate from hydrolysis of plants selected from corn (*Zea mayz* L.), pea (*Pisum sativum*), or rice (*Oryza sativa* L.).

9. The method of claim 1, further comprising isolating said peptidic hydrolyzate from hydrolysis of yeasts of the *Saccharomyces* genus.

10. The method of claim 9, wherein isolating said peptidic hydrolyzate is from *Saccharomyces cerevisiae*.

11. The method of claim 1, wherein said peptidic hydrolyzate contains between 0.5 and 5.5 g/l of the bioactive peptide.

12. The method of claim 1, wherein signs of aging in skin includes wrinkles, deep and coarse wrinkles, fine lines, cracks, the slackening of skin and subcutaneous tissues, the loss of skin elasticity and atony, the loss of firmness and skin tonicity, and dermal atrophy.

* * * * *